(12) United States Patent
Gera et al.

(10) Patent No.: US 9,828,393 B2
(45) Date of Patent: Nov. 28, 2017

(54) SILYLALKYLOXYARYL COMPOUNDS AND METHODS FOR TREATING CANCER

(71) Applicant: THE REGENTS OF THE UNIVERSITY OF COLORADO, a body corporate, Denver, CO (US)

(72) Inventors: Lajos Gera, Centennial, CO (US); Robert S. Hodges, Denver, CO (US); Peter Hegyes, Szeged (HU)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

(21) Appl. No.: 14/907,158

(22) PCT Filed: Jul. 22, 2014

(86) PCT No.: PCT/US2014/047682
§ 371 (c)(1),
(2) Date: Jan. 22, 2016

(87) PCT Pub. No.: WO2015/013322
PCT Pub. Date: Jan. 29, 2015

(65) Prior Publication Data
US 2016/0159832 A1    Jun. 9, 2016

Related U.S. Application Data

(60) Provisional application No. 61/857,192, filed on Jul. 22, 2013.

(51) Int. Cl.
*A61K 31/695* (2006.01)
*C07F 7/08* (2006.01)
*C07F 7/10* (2006.01)
*C07F 9/40* (2006.01)

(52) U.S. Cl.
CPC .............. *C07F 7/10* (2013.01); *C07F 7/0812* (2013.01); *C07F 9/405* (2013.01); *C07F 9/4006* (2013.01)

(58) Field of Classification Search
CPC ....................................................... C07F 7/08
See application file for complete search history.

(56) References Cited

U.S. PATENT DOCUMENTS 6,211,234 B1 *  4/2001  Astles ..................... C07C 43/23
                                                                    514/520

* cited by examiner

*Primary Examiner* — Brian McDowell
(74) *Attorney, Agent, or Firm* — Sheridan Ross P.C.

(57) ABSTRACT

Silylalkyloxyaryl compounds useful as anti-cancer agents. The compounds and pharmaceutical compositions containing them are particularly useful for the treatment of melanoma, colon, neuroblastoma, bladder, breast, lung, pancreatic, melanoma, sarcoma, lymphoma or gastric cancer.

12 Claims, 1 Drawing Sheet

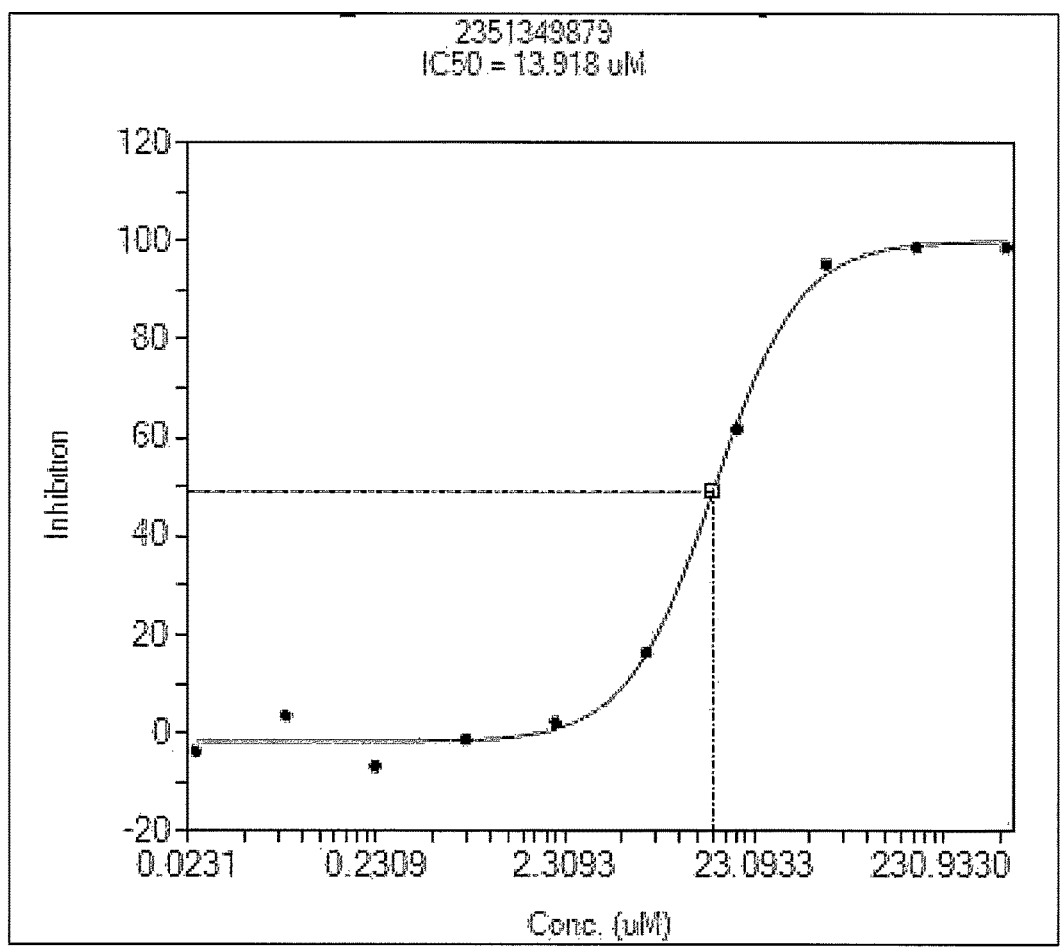

US 9,828,393 B2

SILYLALKYLOXYARYL COMPOUNDS AND METHODS FOR TREATING CANCER

CROSS REFERENCE TO RELATED APPLICATION

This application is a national stage application under 35 U.S.C. 371 of PCT Application No. PCT/US2014/047682 having an international filing date of Jul. 22, 2014, which designated the United States, which PCT application claimed the benefit of U.S. Application Ser. No. 61/857,192, filed Jul. 22, 2013, both of which are incorporated herein by reference, in their entirety.

FIELD OF THE INVENTION

The present invention relates to silylalkyloxyaryl amino acid analog compounds and their use in treating cancers, including melanoma, colon, neuroblastoma, bladder, breast, lung, pancreatic, melanoma, sarcoma, lymphoma or gastric cancer.

BACKGROUND OF THE INVENTION

Adenocarcinoma, arising from the bronchial mucosal glands, is the most frequent non-small cell lung cancer in the United States, representing 35-40% of all lung cancers, and usually occurs in a peripheral location within the lung. Adenocarcinoma is the most common histologic subtype, and may manifest as a "scar carcinoma." This is the subtype observed most commonly in persons who do not smoke and may manifest as multifocal tumors in a bronchoalveolar form.

Bronchoalveolar carcinoma is a distinct subtype of adenocarcinoma with a classic manifestation as an interstitial lung disease on chest radiograph. Bronchoalveolar carcinoma arises from type II pneumocytes and grows along alveolar septa. This subtype may manifest as a solitary peripheral nodule, multifocal disease, or a rapidly progressing pneumonic form. A characteristic finding in persons with advanced disease is voluminous watery sputum.

Squamous cell carcinoma accounts for 25-30% of all lung cancers. The classic manifestation is a cavitary lesion in a proximal bronchus. This type is characterized histologically by the presence of keratin pearls and can be detected based on results from cytologic studies because it has a tendency to exfoliate. It is the type most often associated with hypercalcemia.

Large cell carcinoma accounts for 10-15% of lung cancers, typically manifesting as a large peripheral mass on chest radiograph. Histologically, this type has sheets of highly atypical cells with focal necrosis, with no evidence of keratinization (typical of squamous cell carcinoma) or gland formation (typical of adenocarcinomas).

SUMMARY OF THE INVENTION

In one aspect, the invention includes a silylalkyloxyaryl amino acid analog compound having one of structures:

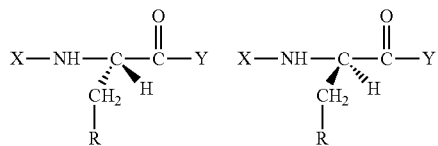

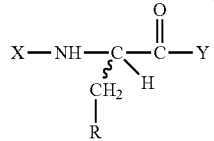

where the structures left-to-right are L, D, and DL amino acid enantiomers,

X is a silylalkyloxyaryl group linked to the amino acid amine group through an amide bond, R is H, or an alkyl, aryl, or heteroaryl group, and Y is $NH_2$, or an NH-alkyl, NH-aryl, NH-alkylaryl, NH-heterocyclic, O-alkyl, O-aryl, or O-alkylaryl group.

In some embodiments the X moiety in the compound may have one of the structures:

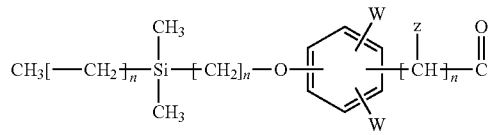

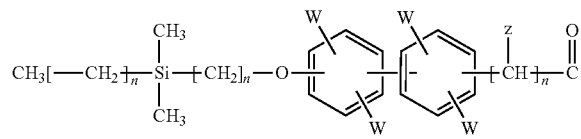

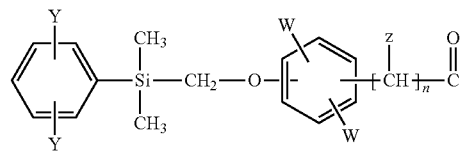

where m: 0-3; n: 1-3; k: 0-1, W is H, alkyl, or halogen, and Z is H, alkyl, or alkyloxy.

Exemplary X moieties include:

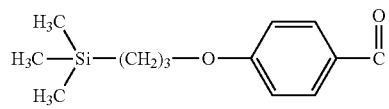

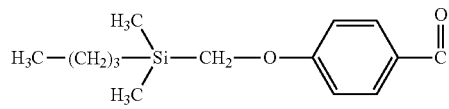

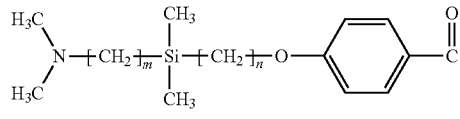

n = 1,3; m = 2,3

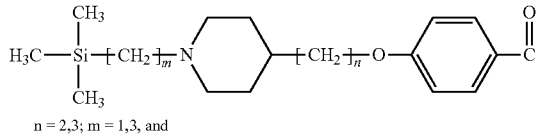

n = 2,3; m = 1,3, and

-continued

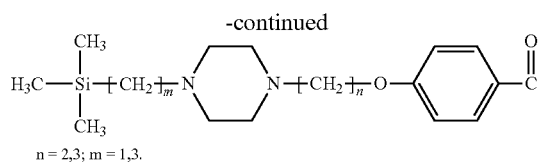

n = 2,3; m = 1,3.

The —NH—CH(CH₂R)—C(O)— moiety (amino acid moiety) may be selected from L-(4-Phenylphenyl)alanine (Bip), L-3,3-Diphenylalanine (Dip), O-(2,6-dicholorbenzyl)-L-tyrosine (OC2Y), L-3-(2-Naphthyl)alanine (2Nal), L-3-Benzothienylalanine (Bta), L-β-Cyclohexylalanine (βCha), L-3-Pyridylalanine (3Pal), L-4-Trifluoromethylphenylalanine (F3MF), L-Fluorophenylalanine (PFF), and L-Melphalane (MEL). Exemplary —NH—CH(CH₂R)—C(O)— moieties include L-(4-Phenylphenyl)alanine (Bip), and O-(2,6-dicholorbenzyl)-L-tyrosine (OC2Y).

The —C(O)Y moiety may be an amide that terminates in a H atom or a 1-6 carbon linear, branched or cyclic alkyl or alkenyl group, including cyclic groups with one or more nitrogen, oxygen or sulfur ring atoms. In exemplary embodiments, Y is 4-Amino-2,2,6,6-tetramethyl piperidine (Atmp) or aminomethylenediphosphonate tetraethyl ester [AMDP (OEt)₄].

Exemplary silylalkyloxyaryl compounds of the invention include compounds given the designation GH1501, GH1502, GH1503, GH1504, and GH1505 by the inventors and which have the following structure:

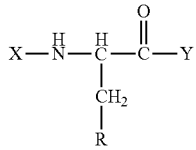

Wherein X, R, and Y groups for each compound are defined within the following table:

| | X | R | Y |
|---|---|---|---|
| GH1501 | H₃C—Si(CH₃)₂—(CH₂)₃—O—C₆H₄—C(O)— | 2,6-dichlorobenzyl-CH₂—O—C₆H₄— | HN—(2,2,6,6-tetramethylpiperidinyl)—NH |
| GH1502 | H₃C—Si(CH₃)₂—(CH₂)₃—O—C₆H₄—C(O)— | biphenyl | HN—(2,2,6,6-tetramethylpiperidinyl)—NH |
| GH1503 | H₃C—(CH₂)₃—Si(CH₃)₂—CH₂—O—C₆H₄—C(O)— | 2,6-dichlorobenzyl-CH₂—O—C₆H₄— | HN—(2,2,6,6-tetramethylpiperidinyl)—NH |
| GH1504 | H₃C—(CH₂)₃—Si(CH₃)₂—(CH₂)₃—O—C₆H₄—C(O)— | biphenyl | HN—(2,2,6,6-tetramethylpiperidinyl)—NH |
| GH1505 | H₃C—Si(CH₃)₂—(CH₂)₃—O—C₆H₄—C(O)— | biphenyl | HN—C(H)[P(O)(OC₂H₅)₂]₂ |

The compounds of the invention may be pure L or pure D enantiomers or a D,L-racemic mixture.

Certain embodiments are pharmaceutical compostions containing at least one of the above silylalkyloxyaryl amino acid analog compounds in a pharmaceutically acceptable medium suitable for administration to a mammal.

Also disclosed is a method of inhibiting the growth or metastasis of cancer cells by exposing the cells to an inhibitory concentration of the silylalkyloxyaryl amino acid analog compound, such as one or more of the exemplary compounds disclosed above. The exposing may result in a 50% inhibition of cell viability at a concentration of compound between 0.1 and 2 μM. The cancer cell line may be selected from a lung (esp. non-small cell lung), head and neck, melanoma, pancreatic, bone, brain (esp neuroblastoma) leukemia, colon, ovarian, renal, prostate, and breast cancer cells.

In a related aspect, the invention includes a method of treating a solid tumor in a mammalian subject, by administering to the subject, a therapeutically effective amount of at least one of the silylalkyloxyaryl amino acid analog compounds of the invention and repeating the administering at intervals of at least twice per week for a period of at least four weeks. The administering may be carried out on a daily basis, every other day or other periodic dosing schedule, at a dose between 0.5 and 25 mg/kg body weight. The compound may be administered orally, intraperitoneally, intravenously, or intra-nasally or by inhalation. The method may further include administering to the patient, a second cancer therapy regimen selected from radiotherapy and one or more other chemotherapeutic compounds. Administering the compound in this combined therapy may be effective to potentiate the effect of the second cancer therapy regimen. For the treatment of pancreatic or lung cancer, the compound may be administered at a daily, every other day or other periodic dosing schedule, at a dose of between 0.5 and 25 mg/kg body weight of the compound over a period of at least fit a five weeks.

These and other objects and features of the invention will be more fully understood from the following detailed description of the invention.

BRIEF DESCRIPTION OF THE DRAWING

FIG. 1 shows the evaluation of enzyme EZH2 inhibitory activity for compound GH1503.

DETAILED DESCRIPTION

I. Definitions

The terms below have the following definitions unless indicated otherwise:

"Pharmaceutically-acceptable salts" refer to derivatives of the disclosed compounds in which the parent compound is modified by making acid or base salts thereof. Examples of pharmaceutically-acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically-acceptable salts are those forms of compounds, suitable for use in contact with the tissues of human beings and animals without causing excessive toxicity, irritation, allergic response, or other problems or complication, commensurate with a reasonable benefit/risk ratio.

The term "solvate" refers to an aggregate of a molecule with one or more solvent molecules. A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of compounds of the present invention, including compounds produced by a process comprising contacting a compound of this invention with a mammal for a period of time sufficient to yield a metabolic product thereof.

The term "therapeutically effective amount" of a compound of this invention means an amount effective to prevent, treat, kill, reduce the growth or inhibit the malignant phenotype of neoplastic cells in a mammalian host.

II. Silylalkyloxyaryl Compounds and Compositions

The present invention is directed to silylalkyloxyaryl anti-cancer compounds and the use of these compounds to treat cancer cells and patients diagnosed with a cancer. The compounds have the general structural formula:

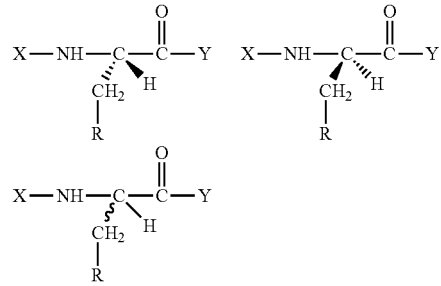

where the structures left-to-right are L, D, and D,L amino acid enantiomers,

X is a silylalkyloxyaryl group linked to NH through an amide bond,

R is H, or an alkyl, aryl, or heteroaryl group, and Y is $NH_2$, or an NH-alkyl, NH-aryl, NH-alkylaryl, NH-heterocyclic, O-alkyl, O-aryl, or O-alkylaryl group. The compound may be a pure L or pure D enantiomer or an D,L racemate at the chiral position shown.

The silylalkyloxyaryl (X) moiety may have one of the following general structures:

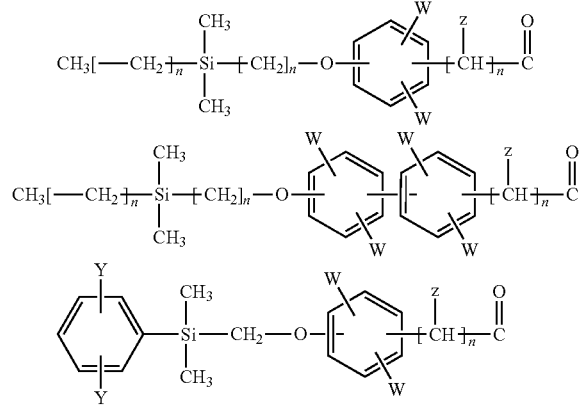

where m is 0-3; n is 1-3; k is 0-1, W is H, alkyl, or halogen, and Z is H, alkyl, or alkyloxy.

Exemplary silylalkyloxyaryl structures include:

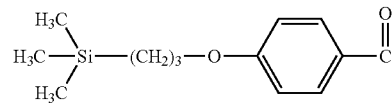

-continued

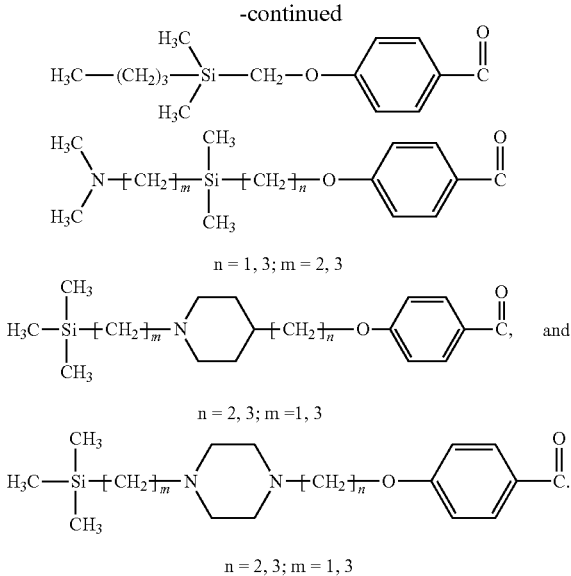

n = 1, 3; m = 2, 3 n = 2, 3; m = 1, 3 n = 2, 3; m = 1, 3

The following list provides exemplary structured natural hydrophobic, hydrophilic α-amino acids and unnatural amino acids (β-amino acids, cyclic, heterocyclic, N-substituted amino acids, etc.), that may form the structure:

—NH—CH(R)—C(O)— within the silylalkyloxyaryl compounds of the invention having the structure:

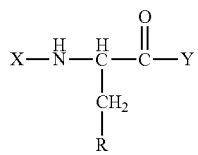

| Abbreviation | Compound |
|---|---|
| Ac6c | 1-Aminocyclohexanecarboxylic acid |
| AcH | 2-Amino-1-cyclohexanecarboxylic acid |
| AcP | 2-Amino-1-cyclopentanecarboxylic acid |
| APa | p-Aminophenylacetic acid |
| Arg | Arginine |
| Atc | 2-aminotetraline-2-carboxylic acid |
| Bip | 4,4'-Biphenylalanine or (4-Phenylphenyl)alanine |
| ChG | α-Cyclohexylglycine |
| CpG | α-Cyclopentyglycine |
| βBpa | β-(p-Biphenylyl)-β-alanine |
| BtA | 3-Benzothienylalanine |
| Dip | 3,3-Diphenylalanine |
| DmK | ε-Dimethyllysine |
| F3MF | 4-Trifluoromethylphenylalanine |
| F5F | Pentafluorophenylalanine |
| Ica | Indoline-2-carboxylic acid |
| Igl | α-2-Indanylglycine |
| MEL | Melphalane |
| 1Nal | 3-(1-Naphthyl)alanine |
| 2Nal | 3-(2-Naphthyl)alanine |
| NiK | ε-Nicotinoyllysine |
| NMF | N-Methylphenylalanine |
| OBPY | O-Benzyl-phosphotyrosine |
| OC2Y | O-(2,6-Dichlorobenzyl)tyrosine |
| OCIY | O-(2,6-Dichlorobenzyl)-3,5-diiodotyrosine |
| Oic | Octahydroindolecarboxylic acid |
| Pac | 4-Aminocinnamic acid |

| Abbreviation | Compound |
|---|---|
| 2Pal | 2-Pyridylalanine |
| 3Pal | 3-Pyridylalanine |
| 4Pal | 4-Pyridylalanine |
| Pen(Mbzl) | S-(4-Methylbenzyl)-penicillamine |
| PaF | p-Amino-phenylalanine |
| PBF | p-Bromo-phenylalanine |
| PCNF | p-Cyano-phenylalanine |
| PgF | p-Guanidino-phenylalanine |
| Phe | Phenylalanine |
| PIF | p-Iodo-phenylalanine |
| PipA | β-3-Piperidylalanine |
| 2Qua | 2-Quinoylalanine |
| 2,4Tfp | 2,4-Bis(trifluoromethyl)-phenylalanine |
| 3Tfp | 3,5-Bis(trifluoromethyl)-phenylalanine |
| Tic | Tetrahydroisoqunoline-3-carboxylic acid |
| Thi | β-(2-Thienyl)-alanine |
| TmK | ε-Trimethyllysine |
| Trp | Tryptophan |
| Tza | 4-Thiazolylalanine |

In one general embodiment, the —C(O)Y moiety within the silylalkyloxyaryl compounds of the invention having the structure:

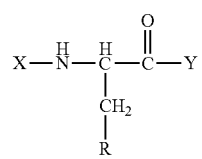

is an amide that terminates in an H atom or a 1-6 carbon linear, branched or cyclic alkyl or alkenyl group, including cyclic groups with one or more nitrogen, oxygen or sulfur ring atoms. Exemplary R groups include:

| Abbreviation | Compound |
|---|---|
| Abzp | 4-Amino-1-benzylpiperidine |
| Acep | 4-Amino-1-carbethoxymethyl-2,2,6,6-tetramethylpiperidine |
| Ambi | 2-(Aminomethyl)benzimidazole |
| AMDP(OEt)4 | Aminomethylenediphosphonate tetraethyl ester |
| Amp | 1-(3-Aminopropyl)-4-methylpiperazine |
| Apia | 4-Amino-piperidine |
| Aptp | 4-Amino-1-(phenylmethyl)-2,2,6,6-tetramethylpiperidine |
| Atmp | 4-Amino-2,2,6,6-tetramethylpiperidine |
| AtmpO | 4-Amino-2,2,6,6-tetramethyl-1-piperidinyloxy |
| Atpc | 4-Amino-2,2,6,6-tetramethyl-4-piperidinecarboxylic acid |
| Atpm | 4-Amino-4-methoxycarbonyl-2,2,6,6-tetramethylpiperidine |
| Aqd | 4-Aminoquinaldine |
| Aqu | (R)-(+)-3-Aminoquinuclidine or (S)-(−)-3-Aminoquinuclidine |
| Bhp | 1-Benzylhomopiperazine |
| Btpha | N,N'-bis(2,2,6,6-Tetramethyl-4-piperidinyl)-1,6-hexanediamine |
| cDmbp | cis-2,6-Dimethyl-1-benzylpiperazine |
| Dabp | Diethyl 4-aminobenzylphosphonate |
| DCE | N,N'-bis(2-Chloroethyl)ethylenediamine |
| Dcpp | 1-(2,3-Diclorophenyl)piperazine |
| Dmm | 2,6-Dimethylmorpholine |
| Dmmp | cis-2,6-Dimethyl-1-(methoxycarbonylmethyl)piperazine |
| Dmpa | 2,6-Dimethyl-4-piperidinamine |
| Ecap | N-(Ethoxycarbonyl)-4-aminopiperidine |
| NH—OH | Hydroxylamine |
| HN(CH₃)(OCH₃) | N,O-Dimethylhydroxylamine |
| Mapp | 4-(Methylamino)-1,2,2,6,6-pentamethylpiperidine |

-continued

| Abbreviation | Compound |
|---|---|
| Matp | 4-(Methylamino)-2,2,6,6-tetramethylpiperidine |
| MatpO | 4-(Methylamino)-2,2,6,6-tetramethyl-1-piperidinyloxy |
| Pipz | Piperazine |
| Pmpz | 1-(2-Pyrimidyl)piperazine |
| Pxa | Pyridoxamine |
| Sua | Sulfanilamide |
| tCip | trans-1-Cinnamylpiperazine |
| Tdpa | Tetrahydro-2,6-dimethyl-2H-pyran-4-amine |
| Tpa | 2,2,6-Trimethyl-4-piperidinamine |
| Tpac | N-(2-aminoethyl)-2,2,5,5-tetramethyl-3-pyrroline-3-carboxamide |
| Tpma | 2,2,6,6-Tetramethyl-4-piperidinemethanamine |
| Tpya | 2,2,5,5-tetramethyl-3-pyrrolidinamine |
| Tpyma | 2,2,5,5-tetramethyl-3-pyrrolidinemethanamine |
| Ttpa | Tetrahydro-2,2,6,6-tetramethyl-2H-pyran-4-amine |

IIA. Exemplary Compounds

Exemplary silylalkyloxyaryl compounds of the invention include compounds given the designation GH1501, GH1502, GH1503, GH1504, and GH1505 by the inventors and which have the following chemical structure:

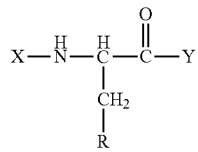

wherein X, R, and Y groups for each compound are defined within the following table:

| | X | R | Y |
|---|---|---|---|
| GH1501 | (CH₃)₃Si—(CH₂)₃—O—C₆H₄—C(=O)— | 2,6-dichlorobenzyloxyphenyl | 2,2,6,6-tetramethylpiperidin-4-ylamino |
| GH1502 | (CH₃)₃Si—(CH₂)₃—O—C₆H₄—C(=O)— | biphenyl | 2,2,6,6-tetramethylpiperidin-4-ylamino |
| GH1503 | CH₃(CH₂)₃Si(CH₃)₂—CH₂—O—C₆H₄—C(=O)— | 2,6-dichlorobenzyloxyphenyl | 2,2,6,6-tetramethylpiperidin-4-ylamino |
| GH1504 | CH₃(CH₂)₃Si(CH₃)₂—CH₂—O—C₆H₄—C(=O)— | biphenyl | 2,2,6,6-tetramethylpiperidin-4-ylamino |
| GH1505 | (CH₃)₃Si—(CH₂)₃—O—C₆H₄—C(=O)— | biphenyl | bis(diethylphosphonate)methylamino |

IIB. Methods of Synthesis

The compounds of the present invention can be synthesized using the methods described in Examples 1A and 1B below, together with synthetic methods known in the art of organic chemistry, or variations thereon as appreciated by those skilled in the art. In each step of preparing the compounds of the present invention, the amino acid derivatives are coupled to the amine derivatives by BOP or HATU in organic solvent to afford the amide derivatives having the structure Boc-NH—CH(CH₂R)—C(O)—Y, wherein R and Y are as defined above. The Boc-groups are cleaved by 25% trifluoroacetic acid (TFA) in DCM and the amino acid-amide derivatives are reacted with the benzoic acid of the silylalkyloxyaryl moiety in the presence of BOP to produce the desired silylalkyloxyaryl amino acid analog compound. A simple extraction is used for the isolation and purification of each intermediate. The final products are purified by crystallization or preparative high pressure liquid chromatography (HPLC) and may be characterized by analytical HPLC, thin layer chromatography (TLC) and laser-desorption mass spectrometry (LDMS).

The reactions are performed in solvents appropriate to the reagents and materials employed and suitable for the transformation being effected. Also, in the description of the synthetic methods described below, it is to be understood that all proposed reaction conditions, including the choice of solvents, reaction temperature, duration of the experiments and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions on the use of substituents that are compatible with the reaction conditions will be readily apparent to one skilled in the art and alternate methods must then be used.

Examples of the synthesis of the compounds of this invention are described in Examples 1A and 1B below, where Example 1A details the synthesis of the GH1502 compound, and Example 1B, details modifications to that synthesis for synthesizing the compounds GH1501, GH1503, GH1504, and GH1505.

Pharmaceutically-acceptable salt forms of compounds provided herein are synthesized from the parent compound which contains a basic or acidic moiety by conventional chemical methods. Generally, such salts are prepared, by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is incorporated herein by this reference.

IIC. Pharmaceutical Compositions

The compounds of the invention are effective in treating cancer over a wide dosage range and are generally administered in a therapeutically-effective amount. The dosage and manner of administration will be defined by the application of the compound and can be determined by routine methods of clinical testing to find the optimum dose. These doses are expected to be in the range of 0.001 mg/kg to 100mg/kg of active compound, preferably 0.5 to 25 mg/kg. It will be understood, however, that the amount of the compound actually administered will be determined by a physician, in the light of the relevant circumstances, including the disease state to be treated, the chosen route of administration, the actual compound administered, the age, weight, and response of the individual patient, the severity of the patient's symptoms, and the like.

When employed as pharmaceuticals, the compounds of the present invention are administered in the form of pharmaceutical compositions and these pharmaceutical compositions represent further embodiments of the present invention. These compounds can be administered by a variety of routes including oral, rectal, transdermal, subcutaneous, intravenous, intramuscular, and intranasal, or via intratracheal instillation or aerosol inhalation.

The pharmaceutical compositions of the present invention contain, as the active ingredient, one or more of the anticancer compounds described above, associated with pharmaceutically acceptable formulations. In making the compositions of this invention, the active ingredient is usually mixed with an excipient, diluted by an excipient or enclosed within a carrier, which can be in the form of a capsule, sachet, paper or other container, according to well-known methods and pharmaceutical compositions.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient, or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

IV. Method of Cancer Treatment

The present invention provides methods of treating cancer in a mammal by administering a therapeutically effective amount of one of the silylalkyloxyaryl compounds of the present invention to the mammal. These methods may include killing or inhibiting the growth of cancer cells in the mammal. These cellular effects result in reduced growth and inhibition of the malignant phenotype of the cell and ultimately, death of the cell. In one aspect, the invention includes a method of inhibiting cancer cells by exposing the cells to an inhibitory concentration of the silylalkyloxyaryl amino acid analog compound of the invention. The data provided in the Examples section of this disclosure demonstrates that method is effective against a wide variety of leukemia, non-small cell lung, colon, CNS, melanoma, ovarian, renal, prostate, and breast cancer cells. Studies conducted with the compounds of the present invention indicate that the compounds of the present invention induce cell death in rapidly dividing cells by apoptosis, rather than cell necrosis.

More generally, the treatment method involves administering to a mammalian subject having a cancer, a therapeutically effective amount of at least one of the silylalkyloxyaryl compounds of the invention, and repeating the compound administration at intervals of at least weekly for a period of at least four weeks. Typically, the compound is administered every day, until a suitable end point, e.g., desired decrease in tumor volume or tumor marker, is achieved. Doses of the compound may range between about 0.5 to 50 mg/kg body weight of the treated subject. For example, the compound may be administered on a daily basis at a daily dose between 1 and 25 mg/kg body weight, typically by oral, intraperitoneal, or intravenous route.

The method may further include administering to the patient a second cancer therapy regimen, such as radiotherapy and/or one or more other chemotherapeutic compounds, where administering the compound of the invention is preferably effective to potentiate the effect of the second cancer therapy regimen. Such additional chemotherapeutic agents may include, for example, acalacinomycin, alitretinoin, allopurinol, altretamine, anastrozole, arsenic trioxide, asparaginase, busulfan, calusterone, camptothecin, capecitabine, carmofur, cladribine, dacarbazine, dexrazoxane, docetaxel, doxifloridine, doxorubicin, dromostanolone, epirubicin, estramustine, etoposide, exemestane, floxuridine, fludarabine, fluorouracil, fulvestrant, gemcitabine, homoharringtonine, hydroxycamptothecin, hydroxyurea, irinotecan, letrozole, levamisole, mesna, mitotane, mitoxantrone, oxaliplatin, paclitaxel, pipobroman, pirarubicin, sarmustine, semustine, tamoxifen, tegafur-uracil, temozotomide, teniposide, testolactone, thioguanine, thiotepa, topotecan, valrubicin, vinblastine, vincristine, vindesine, and vinorelbine.

The methods of treating a mammal with a cancer through the administration of the compounds of the present invention may also include the application of radiation therapy, biological therapy, phototherapy and/or surgery to the mammal In some embodiments, the present invention provides a method for characterizing a cancer tissue in a subject, comprising providing a cancer tissue sample from a subject; and detecting the presence or absence of expression of Enhancer of Zeste Homologue 2 (EZH2), a Histone H3 Lys 27 (H3K27) Methyltransferase, in the sample, thereby characterizing the cancer tissue sample and/or the cancer patient as likely to respond favorably to treatment with a silylalkyloxyaryl compound of the invention.

In some embodiments, detecting the presence of expression of EZH2 comprises detecting the presence of EZH2 mRNA (e.g., including, but not limited to, by exposing the hepsin mRNA to a nucleic acid probe complementary to the hepsin mRNA). In other embodiments, detecting the presence of expression of EZH2 comprises detecting the presence of a EZH2 polypeptide (e.g., including, but not limited to, by exposing the EZH2 polypeptide to an antibody specific to the EZH2 polypeptide and detecting the binding of the antibody to the EZH2 polypeptide). In some embodiments, the subject comprises a human subject. In some embodiments, the sample comprises tumor tissue. In some embodiments, characterizing the cancer tissue comprises identifying a stage of the cancer in the cancer tissue.

In further embodiments, the present invention provides a kit for characterizing cancer in a subject, comprising a reagent capable of specifically detecting the presence of absence of expression of EZH2; and instructions for using the kit for characterizing the cancer in the subject as likely to respond favorably to treatment with a silylalkyloxyaryl compound of the invention.

In some embodiments, the reagent comprises a nucleic acid probe complementary to an EZH2 mRNA. In other embodiments, the reagent comprises an antibody that specifically binds to an EZH2 polypeptide. In certain embodiments, the instructions comprise instructions required by the United States Food and Drug Administration for use in in vitro diagnostic products.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention. Additional objects, advantages, and novel features of this invention will become apparent to those skilled in the art upon examination of the following examples thereof, which are not intended to be limiting.

EXAMPLES

Example 1A

Compound Synthesis

GH1501: $N^\alpha$-{4-[3-(trimethylsilyl)propoxy]-benzoyl}-N-(2,2,6,6-tetramethylpiperidin-4-yl)-[O-(2,6-dichlorobenzyl)-L-tyrosinamide]

GH1502: $N^\alpha$-{4-[3-(trimethylsilyl)propoxy]-benzoyl}-N-(2,2,6,6-tetramethylpiperidin-4-yl)-(4-phenyl-L-phenylalaninamide)

GH1503: $N^\alpha$-{4-[(butyldimethylsilyl)methoxy]-benzoyl}-N-(2,2,6,6-tetramethylpiperidin-4-yl)-[O-(2,6-dichlorobenzyl)-L-tyrosinamide]

GH1504: $N^\alpha$-{4-[(butyldimethylsilyl)methoxy]-benzoyl}-N-(2,2,6,6-tetramethylpiperidin-4-yl)-(4-phenyl-L-phenylalaninamide)

GH1505: $N^\alpha$-{4-[3-(trimethylsilyl)propoxy]-benzoyl}-N-[bis(dietoxyphosphoryl)methyl]-(4-phenyl-L-phenylalaninamide)

This example describes the synthesis of $N^\alpha$-{4-[3-(trimethylsilyl)propoxy]-benzoyl}-N-(2,2,6,6-tetramethylpiperidin-4-yl)-(4-phenyl-L-phenylalaninamide) (GH1502); MSipob-L-Bip-Atmp, $C_{37}H_{51}N_3O_3Si$: 613.92).

To a solution of $N^\alpha$-tert-butoxycarbonyl-4-phenyl-phenylalanine (Boc-L-Bip), $C_{20}H_{23}NO_4$; 341.4 mg, 1.0 mmol), 4-amino-2,2,6,6-tetramethylpiperidine (Atmp, $C_9H_{20}N_2$; 156.27 mg=171.4 µl, 1.0 mmol), and BOP reagent (442.3 mg, 1.0 mmol) in acetonitrile or dimethylformamide (DMF, 25-40 ml) was added N,N-diisopropylethylamine (DIPEA, 348.4 µl, 2.0 mmol). The mixture was stirred at room temperature overnight before the solvent was removed in vacuum. The residue was partitioned between ethyl acetate (75 ml) and water (15 ml). The layers were separated and the organic phase was washed with 5% $KHSO_4$ (3×10 ml), brine (10 ml), 5% $NaHCO_3$ (3×10 ml), brine (10 ml). The organic layer was dried over anhydrous $Na_2SO_4$. The solvent was evaporated, affording a white solid product, (435.2 mg, 90.7%),$N^\alpha$-[(1,1-dimethylethoxy)carbonyl]-N-(2,2,6,6-tetramethylpiperidin-4-yl)-(4-phenyl-L-phenylalaninamide) (Boc-L-Bip-Atmp, $C_{29}H_{41}N_3O_3$: 479.66).

The $N^\alpha$-Boc-group was cleaved according to the classical deprotection procedure. The Boc-compound (239.8 mg, 0.50 mmol) was dissolved in 25% TFA in dichloromethane (DCM, 50 ml). After 30 min. the solution was concentrated under reduced pressure at room temperature and the residue was lyophilized from 25 ml of $H_2O$ to give the crude product as a TFA salt N-(2,2,6,6-tetramethylpiperidin-4-yl)-(4-phenyl-L-phenylalaninamide), 271.9 mg, 89.5%, (L-Bip-Atmp.TFA, $C_{24}H_{33}N_3O$: 379.55+2TFA=607.60) The crude product could be purified by preparative HPLC on a C18 column. The L-Bip-Atmp.2TFA was dissolved in 0.5 N cold HCl (10 ml) and the solution was filtered and lyophilized to obtain the L-Bip-Atmp.2HCl salt (194.5 mg, 96.1%, $C_{24}H_{33}N_3O$: 379.54+2HCl=452.46)

To a stirred mixture of L-Bip-Atmp 2HCl (113.12 mg, 0.25 mmol), 4-[3-(trimethylsilyl)propoxy]-benzoic acid (63.1 mg, 0.25 mmol) and BOP (110.5 mg, 0.25 mmol) in DMF (7.5 ml) was added DIEA (180 µl, 1.0 mmol). The mixture was stirred at room temperature overnight then the solvent was evaporated at reduced pressure. The residue was diluted with ethyl acetate (50 ml) and washed with 5% $KHSO_4$ (3×10 ml), brine (10 ml), 5% $NaHCO_3$ (3×10 ml) and brine (10 ml). After being dried over anhydrous $Na_2SO_4$, the organics were concentrated to dryness yielding the crude MSipob-L-Bip-Atmp. The crude product was purified by preparative HPLC on a C18 column to give the desired product after lyophilization from 50% acetonitrile-$H_2O$. (143.3 mg, 78.74%, as a white solid, Msipob-L-Bip-Atmp.TFA ($C_{37}H_{51}N_3O_3Si$+TFA=727.94).

Example 1B

Modifications of the Methods of 1A for Producing Other Silylalkyloxyaryl Compounds 1. GH1501: $N^\alpha$-{4-[3-(trimethylsilyl)propoxy]-benzoyl}-N-(2,2,6,6-tetramethylpiperidin-4-yl)-[O-(2,6-dichlorobenzyl)-L-tyrosinamide]. This compound was prepared as above, substituting Boc-L-Bip for $N^\alpha$-tert-butoxycarbonyl-[O-(2,6-dichlorobenzyl)-L-tyrosine residue (Boc-L-OC2Y) used in Example 1A.
2. GH1503: $N^\alpha$-{4-[(butyldimethylsilyl)methoxy]-benzoyl}-N-(2,2,6,6-tetramethylpiperidin-4-yl)-[O-(2,6-dichlorobenzyl)-L-tyrosinamide]. This compound was prepared as in Example 1A, substituting Boc-L-Bip residue for Boc-L-OC2Y residue used in Example 1A, and substituting MSipob for the 4-[(butyldimethylsilyl)methoxy]-benzoic acid residue (BmSimob) used in Example 1A.
3. GH1504: $N^\alpha$-{4-[(butyldimethylsilyl)methoxy]-benzoyl}-N-(2,2,6,6-tetramethylpiperidin-4-yl)-(4-phenyl-L-phenylalaninamide). This compound was prepared by substituting MSipob for the BmSimob used in Example 1A.
4. GH1505: $N^{60}$ -{4-[3-(trimethylsilyl)propoxy]-benzoyl}-N-[bis(diethyphosphoryl)methyl]-(4-phenyl-L-phenylalaninamide). This compound was prepared by substituting 4-amino-2,2,6,6-tetramethylpiperidine (Atmp) for the aminomethylenediphosphonate tetraethyl ester [AMDP(OEt)4] used in Example 1A.

Abbreviations
AMDP(OEt)$_4$ aminomethylenediphosphonate tetraethyl ester
Atmp 4-amino-2,2,6,6-tetramethylpiperidine
Bip 4,4'-biphenylalanine or 4-phenyl-phenylalanine
BmSimob 4-[(butyldimethylsilyl)methoxy]-benzoyl
MSipob 4-[3-(trimethylsilyl)propoxy]-benzoyl
OC2Y O-(2,6-dichlorobenzyl)-tyrosine Example 2

Inhibition of Cancer Cell Viability by Silylalkyloxyaryl Amino Acid Analog Compounds Percent cell viability of various cancer and non-cancer cell lines 24 hours after treatment with GH1501, GH1502, GH1503, GH1504, GH1505 and one of 3 groups of non-silyl control amino acid analog compounds was measured by a rapid colorimetric assay based on the tetrazolium salt MTT (3-(4,5-dimethylthiazol-2-yl)-2,5-diphenyl tetrazolium bromide) (Mosmann, J. Immunol. Methods 65: 55-63, 1983, with minor modifications).

In each study, approximately 1,000-5,000 cancer cells from a selected cancer or non-cancer cell line were plated in 100 µl of growth medium in 96-well flat-bottomed microtiter plates. Cells were incubated overnight, followed by addition of one of the eight test compounds at concentrations of 0, 1, 5, 10, and 25 µM. All wells had a final volume of 200 µL. After addition of the test compound, the plates were incubated for 24 hours, then examined for cell viability.

Example 3

NCI-60 Cell Line Testing of Compounds of the Invention

Drug sensitivity data are provided as GI50s (concentrations required to inhibit growth by 50%). The first row of the text file identifies cell lines, separated by tabs. Subsequent rows contain compound number, compound name, and GI50 for each cell line, each separated by a tab.

The NCI-60 cell lines include the following cell lines (tissue of origin is shown in bold):
LUNG: NCI-H23, NCI-H522, A549-ATCC, EKVX, NCI-H226, NCI-H332M, H460, H0P62, HOP92
COLON: HT29, HCC-2998, HCT116, SW620, COL0205, HCT15, KM12
BREAST: MCF7, MCF7ADRr, MDAMB231, HS578T, MDAMB435, MDN, BT549, T47D
OVARIAN: OVCAR3, OVCAR4, OVCAR5, OVCAR8, IGROV1, SKOV3
LEUKEMIA: CCRFCEM, K562, MOLT4, HL60, RPMI8266, SR RENAL: UO31, SN12C, A498, CAKI1, RXF393, 7860, ACHN, TK10
MELANOMA: LOXIMVI, MALME3M, SKMEL2, SKMEL5, SKMEL28, M14, UACC62, UACC257
PROSTATE: PC3, DU145
CNS: SNB19, SNB75, U251, SF268, SF295, SM539

The human tumor cell lines of the NCI cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or one-half log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters are calculated for each experimental agent. Growth inhibition of 50% (GI50) is calculated from $[(Ti-Tz)/(C-Tz)] \times 100 = 50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

The GI50 values for compounds of the invention from the NCI-60 cell line screen are provided in the following table:

| Panel/Cell Line | $GI_{50}$ (nanomolar) | | | |
|---|---|---|---|---|
| | GH1501 | GH1503 | GH1504 | GH1505 |
| Leukemia | | | | |
| CCRF-CEM | 1200 | 531 | 1500 | 2780 |
| HL-60(TB) | 813 | 790 | 1220 | 2940 |
| K-562 | 322 | 333 | 386 | 3460 |
| MOLT-4 | 353 | 315 | 775 | 2860 |
| RPMI-8226 | 1320 | 893 | 1950 | 1970 |
| SR | — | — | — | — |
| Average: | 802 | 572 | 1166 | 2802 |
| Non-Small Cell Lung Cancer | | | | |
| A549/ATCC | 407 | 332 | 326 | 2840 |
| EKVX | — | — | — | — |
| HOP-62 | 1860 | 1510 | 1360 | 2000 |
| HOP-92 | 1170 | 1110 | 1370 | 2090 |
| NCI-H226 | 1770 | 1340 | 183 | 1840 |
| NCI-H23 | 1650 | 1560 | 1760 | 3050 |
| NCI-H322M | 1740 | 1570 | 1710 | 5110 |
| NCI-H460 | 253 | 259 | 348 | 1970 |
| NCI-H522 | 1820 | 1970 | 1060 | 2020 |
| Average: | 1334 | 1206 | 1015 | 2615 |
| Colon Cancer | | | | |
| COLO 205 | 216 | 342 | 215 | 1840 |
| HCC-2998 | 1050 | 1070 | 1110 | 2020 |
| HCT-116 | 206 | 319 | 218 | 1930 |
| HCT-15 | 357 | 323 | 309 | 2250 |
| HT29 | 263 | 342 | 315 | 2020 |
| KM12 | 363 | 382 | 376 | 2610 |
| SW-620 | 313 | 318 | 316 | 2190 |
| Average: | 395 | 442 | 408 | 2123 |
| CNS Cancer | | | | |
| SF-268 | 903 | 611 | 679 | 2070 |
| SF-295 | — | — | — | — |
| SF-539 | 1770 | 1730 | 1770 | 1820 |
| SNB-19 | 1720 | 1600 | 1550 | 2060 |
| SNB-75 | 1340 | 1350 | 1630 | — |
| U-251 | 230 | 234 | 238 | 2090 |
| Average: | 1193 | 1105 | 1173 | 2010 |
| Melanoma | | | | |
| LOX IMVI | 197 | 191 | 207 | 1850 |
| MALME-3M | 1460 | 1200 | 1750 | 1930 |
| M14 | 341 | 334 | 286 | 2100 |
| MDA-MB-435 | 269 | 250 | 292 | 1900 |
| SK-MEL-2 | 1770 | 1560 | 944 | 2110 |
| SK-MEL-28 | 1500 | 1580 | 1330 | 1760 |
| SK-MEL-5 | 1720 | 1680 | 234 | 1580 |
| UACC-257 | 1880 | 1870 | 1780 | 2420 |
| UACC-62 | 1490 | 1500 | 1150 | 1620 |
| Average: | 1181 | 1129 | 886 | 1919 |
| Ovarian Cancer | | | | |
| IGROV1 | 1200 | 704 | 1640 | 3222 |
| OVCAR-3 | 1250 | 761 | 202 | 1870 |
| OVCAR-4 | 1620 | 711 | 521 | 2540 |
| OVCAR-5 | 1680 | 1620 | 1810 | 1710 |
| OVCAR-8 | 268 | 263 | 216 | 2960 |
| NCI/ADR-RES | 1480 | 1250 | 1540 | 3310 |
| SK-OV-3 | 2080 | 2030 | 2120 | 2590 |
| Average: | 1368 | 1048 | 1150 | 2600 |

-continued

| Panel/Cell Line | GI$_{50}$ (nanomolar) | | | |
|---|---|---|---|---|
| | GH1501 | GH1503 | GH1504 | GH1505 |
| Renal Cancer | | | | |
| 786-0 | 369 | 468 | 780 | 2760 |
| A-498 | 1750 | 1950 | 1950 | 3640 |
| ACHN | 1320 | 478 | 402 | 2270 |
| CAKI-1 | 1360 | 1080 | 1580 | 2900 |
| RXF 393 | 1510 | 392 | 179 | 1870 |
| SN12C | 564 | 613 | 526 | 1710 |
| TK-10 | 1850 | 1890 | 1110 | 2500 |
| UO-31 | 1520 | 1500 | 1550 | 2770 |
| Average: | 1280 | 1046 | 1010 | 2553 |
| Prostate Cancer | | | | |
| PC-3 | 1320 | 490 | 1300 | 2100 |
| DU145 | 347 | 274 | 368 | 1930 |
| Average: | 834 | 382 | 834 | 2015 |
| Breast Cancer | | | | |
| MCF-7 | 335 | 356 | 332 | 1880 |
| MDA-MB-231/ATCC | 881 | 494 | 880 | 1620 |
| HS 578T | 1920 | 2010 | 1850 | 2610 |
| BT-549 | 2010 | 2110 | 1960 | 2090 |
| T-47D | 1900 | 1840 | 1820 | 3100 |
| MDA-MB-468 | 1700 | 1540 | 198 | 1720 |
| Average: | 1458 | 1392 | 1173 | 2170 |

Example 4

OIDD Testing of Compounds of the Invention

An organosilicon compound of the invention (GH1503) was tested using the in vitro target-based assays through an open innovation drug discovery program (OIDD). The organosilicon compound tested was given OIDD number 2351349879. As shown in FIG. 1, the OIDD screen indicated that GH1503 is an inhibitor of EZH2 (Enhancer of Zeste Homologue 2), a Histone H3 Lys 27 (H3K27) methyltransferase, with an IC50 in the micromolar range. This enzyme plays a critical role in regulating gene expression and is highly expressed in a wide range of cancer types, including bladder, breast, colon, lung, melanoma, pancreatic cancer, melanoma, sarcoma and lymphomas.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A silylalkyloxyaryl compound having the structure:

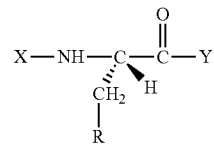

(L)

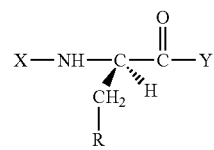

(D)

or

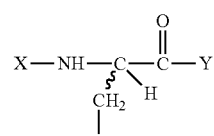

(DL)

wherein, the structures are L, D, and DL amino acid enantiomers, respectively, and, X is a silylalkyloxyaryl group linked to NH through an amide bond, selected from the group consisting of:

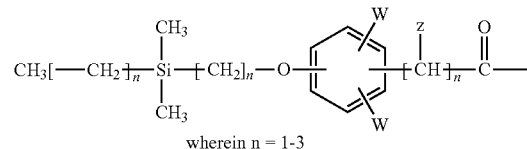

wherein n = 1-3

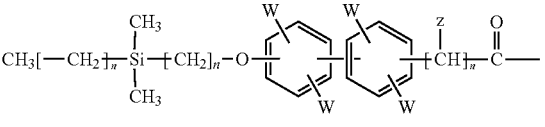

wherein n = 1-3

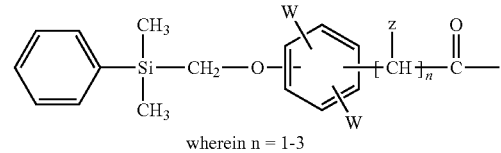

wherein n = 1-3

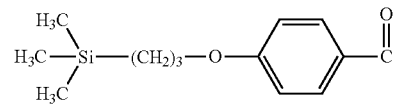

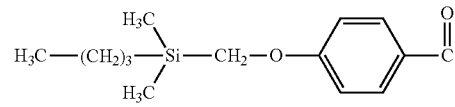

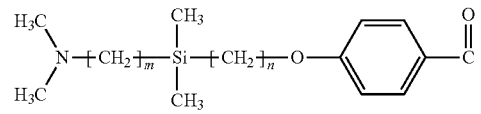

wherein n = 1, 3; m = 2, 3

-continued

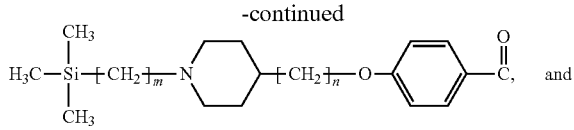

wherein n = 2, 3; m = 1, 3

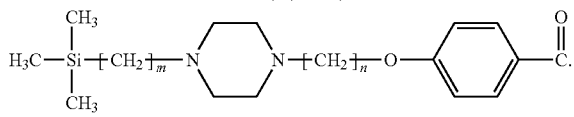

wherein n = 2, 3; m = 1, 3 wherein
W is H, alkyl, or halogen, and
Z is H, alkyl, or alkyloxy,
R is H, or a substituted or unsubstituted alkyl, aryl, or heteroaryl group, and
Y is substituted or unsubstituted NH$_2$, NH-alkyl, NH-aryl, NH-alkylaryl, or NH-heterocyclic group.

2. The compound of claim 1, wherein X is selected from the group consisting of:

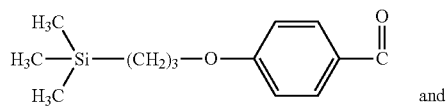

and

-continued

3. The compound of claim 1, wherein R is selected from the group consisting of
4-phenyl-phenyl,
diphenyl,
phenyl-O-(2,6-dicholorbenzyl),
naphthyl,
3-benzothienyl,
cyclohexyl,
3-Pyridyl,
4-trifluoromethylphenyl,
fluorophenyl, and
melphalan.

4. The compound of claim 1, wherein Y is 4-Amino-2,2,6,6-tetramethylpiperidine (Atmp) or aminomethylenediphosphonate tetraethyl ester [AMDP(OEt)$_4$].

5. A silylalkyloxyaryl compound of claim 1
wherein X, R, and Y groups are selected from:

| X | R | Y |
|---|---|---|
| GH1501 | 2,6-dichlorobenzyl-CH$_2$-O-phenyl | HN-2,2,6,6-tetramethylpiperidin-4-yl-NH |
| GH1502 | 4-phenyl-phenyl | HN-2,2,6,6-tetramethylpiperidin-4-yl-NH |
| GH1503 | 2,6-dichlorobenzyl-CH$_2$-O-phenyl | HN-2,2,6,6-tetramethylpiperidin-4-yl-NH |
| GH1504 | 4-phenyl-phenyl | HN-2,2,6,6-tetramethylpiperidin-4-yl-NH |

| X | R | Y |
|---|---|---|
| 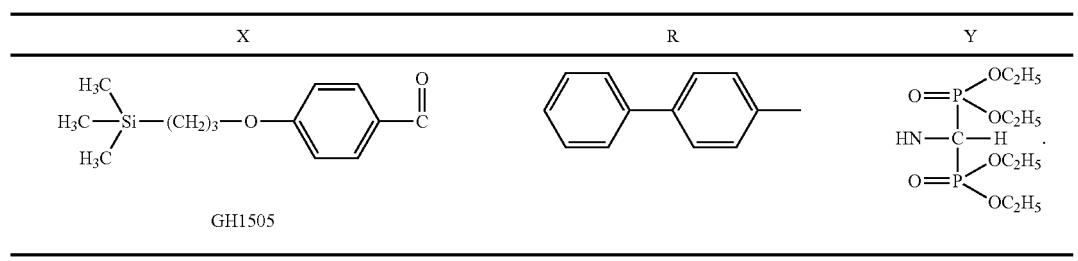 GH1505 | | |

6. A pharmaceutical composition containing the compound of claim 1 in a pharmaceutically acceptable medium suitable for oral or parenteral administration.

7. A method of treating a solid tumor in a mammalian subject, comprising administering to the subject, a therapeutically effective amount of a compound of claim 1, and repeating said administration at intervals of at least once weekly for a period of at least four weeks.

8. The method of claim 7, wherein said compound is administered daily at a daily dose between 0.5 and 25 mg/kg body weight.

9. The method of claim 7, wherein said compound is administered orally, intraperitoneally, intravenously, intranasally or by inhalation.

10. The method of claim 7, which further includes administering to the patient a second cancer therapy regimen selected from radiotherapy and one or more other chemotherapeutic compounds.

11. The method of claim 10, wherein administering the compound is effective to potentiate the effect of the second cancer therapy regimen.

12. The method of claim 7, wherein the tumor is at least one of pancreatic or lung cancer, and wherein said administering includes administering the compound at a daily dose between 0.5 and 25 mg/kg body weight of the compound over a period of at least five weeks.

* * * * *